(12) United States Patent  
Schwartz

(10) Patent No.: US 7,877,128 B2  
(45) Date of Patent: Jan. 25, 2011

(54) SIMULATION OF INVASIVE PROCEDURES

(75) Inventor: Yitzhack Schwartz, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 632 days.

(21) Appl. No.: 11/195,050

(22) Filed: Aug. 2, 2005

(65) Prior Publication Data  
US 2007/0043285 A1 Feb. 22, 2007

(51) Int. Cl.  
A61B 5/05 (2006.01)

(52) U.S. Cl. .................. 600/407; 600/409; 600/424; 600/443; 600/463

(58) Field of Classification Search .................. 600/437, 600/407, 409, 424, 427, 443, 463, 467  
See application file for complete search history.

(56) References Cited

U.S. PATENT DOCUMENTS

| | | | | |
|---|---|---|---|---|
| 5,391,199 | A * | 2/1995 | Ben-Haim | 607/122 |
| 5,445,166 | A * | 8/1995 | Taylor | 128/897 |
| 5,718,241 | A | 2/1998 | Ben-Haim et al. | |
| 5,733,259 | A * | 3/1998 | Valcke et al. | 604/66 |
| 5,871,018 | A * | 2/1999 | Delp et al. | 128/898 |
| 5,873,822 | A * | 2/1999 | Ferre et al. | 600/407 |
| 5,928,248 | A * | 7/1999 | Acker | 623/1.11 |
| 5,951,571 | A * | 9/1999 | Audette | 606/130 |
| 5,954,665 | A * | 9/1999 | Ben-Haim | 600/515 |
| 5,967,980 | A * | 10/1999 | Ferre et al. | 600/424 |
| 5,987,345 | A * | 11/1999 | Engelmann et al. | 600/407 |
| 6,146,390 | A * | 11/2000 | Heilbrun et al. | 606/130 |
| 6,148,095 | A * | 11/2000 | Prause et al. | 382/131 |
| 6,241,657 | B1 * | 6/2001 | Chen et al. | 600/117 |
| 6,368,285 | B1 * | 4/2002 | Osadchy et al. | 600/508 |
| 6,379,302 | B1 * | 4/2002 | Kessman et al. | 600/437 |
| 6,389,311 | B1 * | 5/2002 | Whayne et al. | 600/523 |
| 6,522,908 | B1 * | 2/2003 | Miyashita et al. | 600/409 |
| 6,538,634 | B1 * | 3/2003 | Chui et al. | 345/156 |
| 6,547,782 | B1 | 4/2003 | Taylor | |
| 6,575,969 | B1 * | 6/2003 | Rittman et al. | 606/41 |
| 6,580,938 | B1 * | 6/2003 | Acker | 600/424 |
| 6,650,927 | B1 * | 11/2003 | Keidar | 600/424 |
| 6,673,453 | B2 * | 1/2004 | Beavers et al. | 428/420 |
| 7,263,397 | B2 * | 8/2007 | Hauck et al. | 600/374 |
| 7,286,866 | B2 * | 10/2007 | Okerlund et al. | 600/407 |

(Continued)

OTHER PUBLICATIONS

U.S. Appl. No. 11/114,847, Biosense Webster, Inc., pending.

(Continued)

Primary Examiner—Brian Casler  
Assistant Examiner—Baisakhi Roy  
(74) Attorney, Agent, or Firm—Louis J. Capezzuto

(57) ABSTRACT

A method for pre-planning and performing a cardiac procedure on a heart includes acquiring an image or map of the heart; displaying the image or map of the heart; marking at least one feature on the image or map; calculating dimensions of the at least one feature; identifying one or more points on or within the heart for treatment; determining paths to the one or more points on or within the heart for treatment; simulating insertion of a sheath into the heart; simulating insertion of a medical device through the sheath and within the heart; verifying that the one or more points on or within the heart can be accessed for treatment; and performing a medical procedure on or within the heart.

17 Claims, 7 Drawing Sheets

U.S. PATENT DOCUMENTS

| | | | | |
|---|---|---|---|---|
| 7,536,216 | B2* | 5/2009 | Geiger et al. | 600/407 |
| 2002/0040220 | A1 | 4/2002 | Zvuloni et al. | |
| 2002/0168618 | A1* | 11/2002 | Anderson et al. | 434/262 |
| 2003/0029464 | A1* | 2/2003 | Chen et al. | 128/922 |
| 2003/0053697 | A1 | 3/2003 | Aylward et al. | |
| 2003/0069719 | A1* | 4/2003 | Cunningham et al. | 703/7 |
| 2003/0208116 | A1* | 11/2003 | Liang et al. | 600/407 |
| 2004/0087850 | A1* | 5/2004 | Okerlund et al. | 600/407 |
| 2004/0153128 | A1* | 8/2004 | Suresh et al. | 607/14 |
| 2004/0225331 | A1 | 11/2004 | Okerlund et al. | |
| 2005/0018885 | A1* | 1/2005 | Chen et al. | 382/128 |
| 2005/0053267 | A1* | 3/2005 | Mostafavi | 382/128 |
| 2005/0090742 | A1* | 4/2005 | Mine et al. | 600/443 |
| 2005/0182319 | A1* | 8/2005 | Glossop | 600/424 |
| 2005/0277823 | A1* | 12/2005 | Sutherland et al. | 600/407 |
| 2006/0116576 | A1* | 6/2006 | McGee et al. | 600/434 |
| 2006/0173293 | A1* | 8/2006 | Marquart et al. | 600/426 |
| 2007/0014452 | A1* | 1/2007 | Suresh et al. | 382/128 |
| 2007/0032826 | A1* | 2/2007 | Schwartz | 607/2 |
| 2007/0043285 | A1* | 2/2007 | Schwartz | 600/407 |
| 2007/0043296 | A1* | 2/2007 | Schwartz | 600/463 |
| 2007/0167718 | A1* | 7/2007 | Kaufman et al. | 600/407 |
| 2007/0293734 | A1* | 12/2007 | Coste-Maniere et al. | 600/300 |

OTHER PUBLICATIONS

U.S. Appl. No. 11/195,123, Biosense Webster, Inc., pending.

U.S. Appl. No. 11/195,235, Biosense Webster, Inc., pending.

Alessie, Maurits et al. Electrical, Contractile and Structural Remodeling During Atrial Fibrillation, Cardiovascular Research, vol. 54, Issue 2, May 2002, pp. 230-246.

Ausma, Jannie PhD et al. Reverse Structural and Gap-Junctional Remodeling After Prolonged Atrial Fibrillation in the Goat, Circulation, 2003;107:2051-2058.

Chen, Shih-Ann et al. Pathophysiology of the Pulmonary Vein as an Atrial Fibrillation Initiator: From Bench to Clinic, Pace 2003, 26[Pt. II]:1576-1582.

Epstein, L.M. et al. Nonfluroscopic Transseptal Catheterization: Safety and Efficacy of Intracardiac Echocardiographic Guidance, Cardiovascular Division, Beth Israel Deaconess Medical Center, Harvard Medical School, PMID: 9654229.

Haissaguerre, Michel et al. Spontaneous Initiation of Atrial Fibrillatin by Ectopic Beats Originating in the Pulmonary Veins, New England Journal of Medicine, vol. 339, No. 10, pp. 659-666, Sep. 3, 1998.

Hocini, Meleze, M.D., et al. Techniques for Curative Treatment of Atrial Fibrillation, Journal Cardiovascular Electrophysiology, Techniques and Technology, vol. 15, pp. 1467-1471, Dec. 2004.

Jais, Pierre, M.D. et al. Technique and Results of Linear Ablation at the Miral Isthmus, Circulation, 2004;110:2996-3002.

Jalife, Jose, M.D. Rotors and Spiral Waves in Atrial Fibrillation, Journal Cardiovascular Electrophysiology, vol. 14, pp. 776-780, Jul. 2003.

Khoury D.S. et al. Localizing and Quantifying Ablation Lesions in the Left Ventricle by Myocardial Contrast Echocardiography, Journal of Cardiovascular Electrophysiology, Mar 12, 2001 (3):343-8.

Khoury D.S. et al. Localizing and Quantifying Ablation Lesions in the Left Ventricle by Myocardial Contrast Echocardiography, Journal of Cardiovascular Electrophysiology, vol. 15, Issue 9, p. 1078, Sep. 2004.

Lemola, Kristina, M.D. Effects of Left Atrial Ablation of Atrial Fibrillation on Size of the Left Atrium and Pulmonary Veins, Heart Rhythm 2004;1:576-581.

Lesh M.D. et al. Use of Intracardiac Echocardiography During Electrophysiologic Evaluation and Therapy of Atrial Arrhythmias, J. Cardiovasc. Electrophysiol. Aug. 1998;9 (8 Suppl): S40-7.

McAnulty, John, M.D. Probing for Mechanisms of Atrial Fibrllation: Pulmonary Vein Ostia, Journal of Cardiovascular Electrophysiology, vol. 16, p. 6, Jan. 2005.

Morton, J.B. et al. Phased-Array Intracardiac Echocardiography to Guide Radiofrequency Ablation in the Left Atrium and at the Pulmonary Vein Ostium, J. Cardiovasc. Electrophysiol. Aug. 1998; 9 (8 Suppl):S40-7.

Nattel, Stanley, New Ideas About Atrial Fibrillation 50 Years on, Nature, vol. 415;219-226, Jan. 10, 2002.

Pappone, Carlo, M.D. et al. Atrial Electroanatomic Remodeling After Circumferential Radiofrequency Pulmonary Vein Ablation, Circulation, 2001;104:2539-2544.

Pappone, Carlo, M.D. et al. Mortality, Morbidity, and Quality of Life After Circumferential Pulmonary Vein Ablation for Atrial Fibrillation, Journal of the Americal College of Cardiology, vol. 42, No. 2, 2003;185-197.

Ravelli, Flavia, PhD et al. Effects of Atrial Dilatation on Refractory Period and Vulnerability to Atrial Fibrillation in the Isolated Langendorff-Perfused Rabbit Heart. Circulation, 1997;96:1686-1695.

Schotten, Ulrich, M.D. Electrical and Contractile Remodeling During the First Days of Atrial Fibrillation Go Hand in Hand, Circulation, 2003;107:1433-1439.

Tsao, Hsuan-Ming, M.D. et al. Morphologic Remodeling of Pulmonary Veins and Left Atrium After Catheter Ablation of Atrial Fibrillation: Insight From Long-Term Follow-Up and Three-Dimensional Magnetic Resonance Imaging, Journal Cardiovascular Electrophysiology, vol. 16, pp. 7-12, Jan. 2005.

Waldo, Albert L., M.D. Mechanisms of Atrial Fibrillation, Journal Cardiovascular Electrophysiology, vol. 14, pp. S267-S274, Dec. 2003, suppl.

Wijffels, C.E.F. Maurits et al. Atrial Fibrillation Begets Atrial Fibrillation a Study in Awake Chronically Instrumented Goats, Circulation, 1995;92:1954-1968.

Wittkampf, Fred H.M. PhD et al. Pulmonary Vein Ostium Geometry Analysis by Magnetic Resonance Angiography, Circulation, 2003;107:1-3.

Wu, Tsu-Juey PhD et al. Atrial Fibrillation: Focal Activity, Re-Entry, or Both? Heart Rhythm (2004) 1, 117-120.

Breeuwer, M. et al. The Easi Project—Improving the Effectiveness and Quality of Image-Guided Surgery, IEEE Transactions on Information Technology in Biomedicine, vol. 2 No. 3.Sep. 1998, pp. 156-168.

Hastenteufel, M. et al. Ultrasound-Based Navigation for Minimally Invasive Surgical Atrial Fibrillation Treatment: Workflow and Application Prototype, Medical Imaging 2005: Visualization, Image-Guided Procedures, and Display, Proc of SPIE, vol. 5744, 2005, pp. 400-407.

* cited by examiner

SIMULATION OF INVASIVE PROCEDURES

FIELD AND BACKGROUND OF THE INVENTION

The present invention relates, in general, to the planning and implementing of medical procedures, and, in particular, to a new and useful method for planning, simulating and conducting a medical procedure such as a cardiac treatment procedure as well as a new and useful systematic method for treating atrial fibrillation under ultrasound guidance and a new and useful method for planning, simulating and conducting a medical procedure for preventing macro-reentrant circuits from occurring in the atrium of the heart.

As is well known in the medical field, atrial fibrillation is a major disease state and is characterized as a common sustained cardiac arrhythmia and is widely known to be a major cause of stroke. This condition is perpetuated by reentrant wavelets, such as macro-reentrant circuits, propagating in an abnormal atrial-tissue substrate with conduction heterogeneity and altered refractory period. Various approaches have been developed to interrupt these macro-reentrant circuits wavelets, including surgical or catheter-mediated atriotomy.

A common approach for treating atrial fibrillation is through the use of radio-frequency (RF) ablation energy using an ablation catheter. In using an RF ablation catheter, continuous linear lesions are formed by ablation in order to segment the heart tissue of the atrium. By segmenting the heart tissue, no electrical activity can be transmitted from one segment to another. Preferably, the segments are made very small in order to be able to sustain the fibrillatory process.

As a result, several catheter ablation techniques may be used to treat atrial fibrillation by ablating lines in the left atrium. The relevant anatomical features involved in this type of procedure are schematically illustrated in FIG. 1B. Typically, for this purpose, the physician attempts to ablate lines in the left atrium 10 around the ostia of the pulmonary veins (13, 14, 16 and 18), in order to isolate foci of the arrhythmia. The physician may also ablate lines along the mitral isthmus connecting the right inferior pulmonary vein to the mitral valve 20 and/or the left atrial appendage ridge between the left superior pulmonary vein and the left atrial appendage 22.

And, as can be greatly appreciated, ablation of structures in the left atrium can be a very complex and even tricky procedure and is heavily dependent upon the individual skill of the operating physician. Part of the procedure complexity includes accessing the left atrium 10 in an efficient and safe manner. Thus, in order to properly reach or access the left atrium 10, the physician must pass a sheath 40 through the vena cava into the right atrium, and then through the interatrial septum 11 at fossa ovalis 12 and into the left atrium 10. The physician then must pass an ablation catheter 50 through the sheath 40 into the left atrium 10, and must then position the catheter 50 at a succession of locations that define the ablation lines. The procedure is shown schematically in FIG. 1B. Optimal deployment of the sheath 40 and catheter 50 for these purposes varies substantially from patient to patient, due to a high level of anatomical variability. Failure to position and operate the medical devices or procedure tools correctly may result, at the least, in failure to fully isolate a focus of the arrhythmia, and can cause fatal complications. As a result, left atrial ablation has a sub optimal success rate.

SUMMARY OF THE INVENTION

The present invention is directed to several novel inventions to include methods for planning and implementing medical procedures. In particular, one novel method in accordance with the present invention is directed to a new and useful method for planning, simulating and conducting a medical procedure such as a cardiac treatment procedure. Another novel method in accordance with the present invention is directed to a new and useful systematic method for treating atrial fibrillation under ultrasound guidance. Additionally, another novel method in accordance with the present invention is directed to a new and useful systematic method for planning, simulating and conducting an atrial fibrillation procedure under ultrasound guidance. A further novel method in accordance with the present invention is directed to a new and useful method for planning, simulating and conducting a medical procedure for preventing macro-reentrant circuits from occurring in the atrium of the heart.

In accordance with one invention of the present invention, a method for pre-planning a cardiac procedure on a heart comprises the steps of:
acquiring an image or map of the heart;
displaying the image or map of the heart;
marking at least one feature on the image or map;
calculating dimensions of the at least one feature;
identifying one or more points on or within the heart for treatment;
determining paths to the one or more points on or within the heart for treatment;
simulating insertion of a sheath into the heart;
simulating insertion of a medical device through the sheath and within the heart; and
verifying that the one or more points on or within the heart can be accessed for treatment.

In accordance with another embodiment of the present invention, a method for developing a plan for a cardiac procedure comprises the steps of:
acquiring an image or map of the heart;
displaying the image or map of the heart;
marking at least one feature on the image or map;
calculating dimensions of the at least one feature;
identifying one or more points on or within the heart for treatment;
determining paths to the one or more points on or within the heart for treatment;
simulating insertion of a sheath into the heart;
simulating insertion of a medical device through the sheath and within the heart; and
verifying that the one or more points on or within the heart can be accessed for treatment.

Another embodiment in accordance with the present invention is a method for pre-planning and performing a cardiac procedure on a heart comprising the steps of:
acquiring an image or map of the heart;
displaying the image or map of the heart;
marking at least one feature on the image or map;
calculating dimensions of the at least one feature;
identifying one or more points on or within the heart for treatment;
determining paths to the one or more points on or within the heart for treatment;
simulating insertion of a sheath into the heart;
simulating insertion of a medical device through the sheath and within the heart;
verifying that the one or more points on or within the heart can be accessed for treatment; and
performing a medical procedure on or within the heart.

A further embodiment according to the present invention is a method for developing a plan and performing a cardiac procedure on a heart comprising the steps of:

acquiring an image or map of the heart;
displaying the image or map of the heart;
marking at least one feature on the image or map;
calculating dimensions of the at least one feature;
identifying one or more points on or within the heart for treatment;
determining paths to the one or more points on or within the heart for treatment;
simulating insertion of a sheath into the heart;
simulating insertion of a medical device through the sheath and within the heart;
verifying that the one or more points on or within the heart can be accessed for treatment; and
performing a medical procedure on or within the heart.

Additionally, another embodiment of the present invention is a method for simulating a cardiac procedure on a heart comprising the steps of:
acquiring an image or map of the heart;
displaying the image or map of the heart;
marking at least one feature on the image or map;
calculating dimensions of the at least one feature;
identifying one or more points on or within the heart for treatment;
determining paths to the one or more points on or within the heart for treatment;
simulating insertion of a sheath into the heart;
simulating insertion of a medical device through the sheath and within the heart; and
verifying that the one or more points on or within the heart can be accessed for treatment.

Also, another embodiment according to the present invention is a method for simulating and developing a plan for a cardiac procedure comprising the steps of:
acquiring an image or map of the heart;
displaying the image or map of the heart;
marking at least one feature on the image or map;
calculating dimensions of the at least one feature;
identifying one or more points on or within the heart for treatment;
determining paths to the one or more points on or within the heart for treatment;
simulating insertion of a sheath into the heart;
simulating insertion of a medical device through the sheath and within the heart; and
verifying that the one or more points on or within the heart can be accessed for treatment.

Moreover, another embodiment of the present invention is directed to a method for simulating and performing a cardiac procedure on a heart comprising the steps of:
acquiring an image or map of the heart;
displaying the image or map of the heart;
marking at least one feature on the image or map;
calculating dimensions of the at least one feature;
identifying one or more points on or within the heart for treatment;
determining paths to the one or more points on or within the heart for treatment;
simulating insertion of a sheath into the heart;
simulating insertion of a medical device through the sheath and within the heart;
verifying that the one or more points on or within the heart can be accessed for treatment; and
performing a medical procedure on or within the heart.

Furthermore, another embodiment of the present invention is a method for simulating a cardiac procedure, developing a plan and performing a cardiac procedure on a heart comprising the steps of:
acquiring an image or map of the heart;
displaying the image or map of the heart;
marking at least one feature on the image or map;
calculating dimensions of the at least one feature;
identifying one or more points on or within the heart for treatment;
determining paths to the one or more points on or within the heart for treatment;
simulating insertion of a sheath into the heart;
simulating insertion of a medical device through the sheath and within the heart;
verifying that the one or more points on or within the heart can be accessed for treatment; and
performing a medical procedure on or within the heart.

Another invention according to the present invention is directed to a method for treating atrial fibrillation in a heart of a patient, comprising the steps of:
placing an ultrasonic catheter in a first chamber of the heart;
acquiring three-dimensional ultrasonic image slices of a second chamber of the
heart and at least a portion of surrounding structures of the second chamber using
the ultrasonic catheter placed in the first chamber;
reconstructing a three-dimensional ultrasonic image reconstruction based on the
three-dimensional ultrasonic image slices;
displaying the three-dimensional ultrasonic image reconstruction;
identifying at least one key landmark on the three-dimensional ultrasonic image reconstruction;
marking the least one key landmark on the three-dimensional ultrasonic image reconstruction;
penetrating the septum for accessing the second chamber of the heart while using the marked at least one key landmark for guidance;
positioning a sheath through the penetrated septum and within the second chamber of the heart;
inserting an ablation catheter through the sheath and into the second chamber of the heart; and
ablating a portion of the second chamber of the heart using the ablation catheter while under observation with the ultrasound catheter located in the first chamber of the heart.

Additionally, another embodiment of the invention is a method for simulating, developing a plan and treating atrial fibrillation in a heart of a patient, comprising the steps of:
placing an ultrasonic catheter in a first chamber of the heart;
acquiring three-dimensional ultrasonic image slices of a second chamber of the
heart and at least a portion of surrounding structures of the second chamber using
the ultrasonic catheter placed in the first chamber;
reconstructing a three-dimensional ultrasonic image reconstruction based on the
three-dimensional ultrasonic image slices;
displaying the three-dimensional ultrasonic image reconstruction;
identifying at least one key landmark on the three-dimensional ultrasonic image reconstruction;
marking the least one key landmark on the three-dimensional ultrasonic image reconstruction;
identifying one or more points for treatment on the three-dimensional ultrasonic image reconstruction;
determining paths to the one or more points for treatment using the marked at least one key landmark as a guide;

simulating on the three-dimensional ultrasonic image reconstruction insertion of a sheath into the heart;

simulating on the three-dimensional ultrasonic image reconstruction insertion of a medical device through the sheath and within the second chamber of the heart;

verifying that the one or more points for treatment in the second chamber of the heart can be accessed for treatment;

outlining a plan based on the simulation;

using the plan, penetrating the septum of the heart for accessing the second chamber of the heart;

positioning a sheath through the penetrated septum and within the second chamber of the heart;

inserting an ablation catheter through the sheath and into the second chamber of the heart; and ablating a portion of the second chamber of the heart using the ablation catheter while under observation with the ultrasound catheter located in the first chamber of the heart.

Furthermore, the present invention is also directed to a method for preventing macro-reentrant circuits from occurring in a portion of a heart of a patient, comprising the steps of:

(a) acquiring an image or map of the portion of the heart;
(b) displaying the image or map of the portion of the heart;
(c) marking at least one feature on the image or map;
(d) calculating dimensions of the at least one feature;
(e) identifying one or more points on or within the heart for treatment as part of a treatment plan;
(f) determining paths to the one or more points on or within the heart for treatment;
(g) simulating insertion of a sheath into the heart;
(h) simulating insertion of a medical device through the sheath and within the heart;
(i) verifying that the one or more points on or within the heart can be accessed for treatment;
(j) computing an overall surface area of the portion of the heart;
(k) calculating an estimated area not treated in the portion of the heart based on the treatment plan;
(l) assessing whether macro-reentrant circuits can exist in the estimated area not treated in the portion of the heart;
(m) repeating steps (e)-(l) in the event step (l) indicates that macro-reentrant circuits can exist in the estimated area not treated in the portion of the heart; and
(n) implementing the treatment plan.

Another embodiment of this invention in accordance with the present invention is a method for treating atrial fibrillation in an atrium of a heart of a patient, comprising the steps of:

(a) acquiring an image or map of the atrium;
(b) displaying the image or map of the atrium;
(c) marking at least one feature on the image or map;
(d) calculating dimensions of the at least one feature;
(e) identifying one or more points on or within the atrium for treatment as part of a treatment plan;
(f) determining paths to the one or more points on or within the atrium for treatment;
(g) simulating insertion of a sheath into the atrium;
(h) simulating insertion of a medical device through the sheath and into the atrium;
(i) verifying that the one or more points on or within the atrium can be accessed for treatment;
(j) computing an overall surface area of the atrium;
(k) calculating an estimated area not treated in the atrium based on the treatment plan;
(l) assessing whether macro-reentrant circuits can exist in the estimated area not treated in the atrium;
(m) repeating steps (e)-(l) in the event step (l) indicates that macro-reentrant circuits can exist in the estimated area not treated in the atrium; and
(n) implementing the treatment plan.

BRIEF DESCRIPTION OF THE DRAWINGS

The novel features of the invention are set forth with particularity in the appended claims. The invention itself, however, both as to organization and methods of operation, together with further objects and advantages thereof, may be understood by reference to the following description, taken in conjunction with the accompanying drawings in which:

DESCRIPTION OF THE PREFERRED EMBODIMENTS

The present invention relates to several novel methods for planning and implementing medical procedures. In particular, one novel method in accordance with the present invention is directed to a new and useful method for planning, simulating and conducting a medical procedure such as a cardiac treatment procedure. Another novel method in accordance with the present invention is directed to a new and useful systematic method for treating atrial fibrillation under ultrasound guidance. Yet another novel method in accordance with the present invention is directed to a new and useful systematic method for planning, simulating and conducting an atrial fibrillation procedure under ultrasound guidance. A further novel method in accordance with the present invention is directed to a new and useful method for planning, simulating and conducting a medical procedure for preventing macro-reentrant circuits from occurring in the atrium of the heart.

Figure 1A:
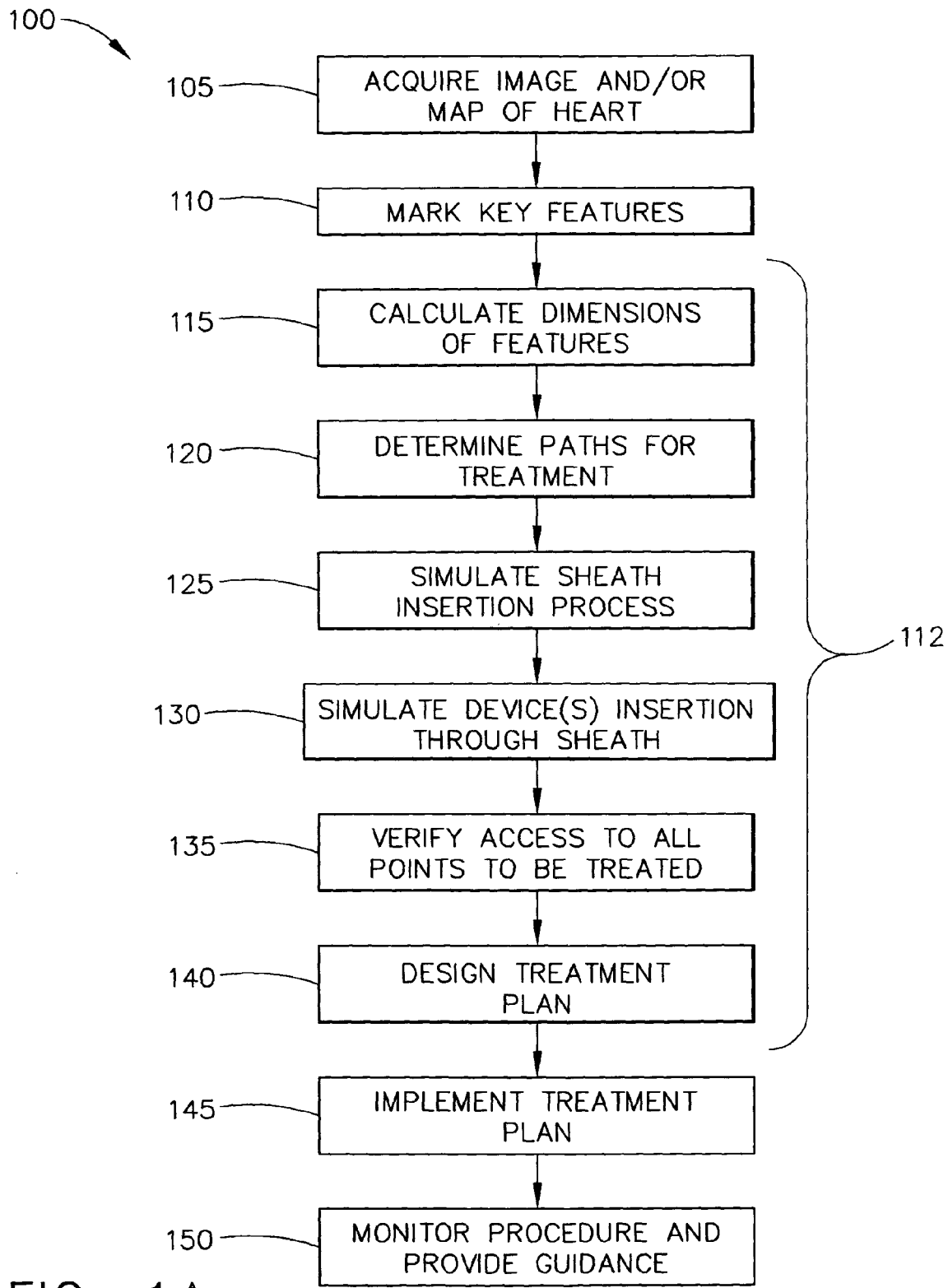
FIG. 1A is a flow chart illustrating a method for simulating, planning and implementing a medical procedure in accordance with one embodiment of the present invention.
Figure 1B:
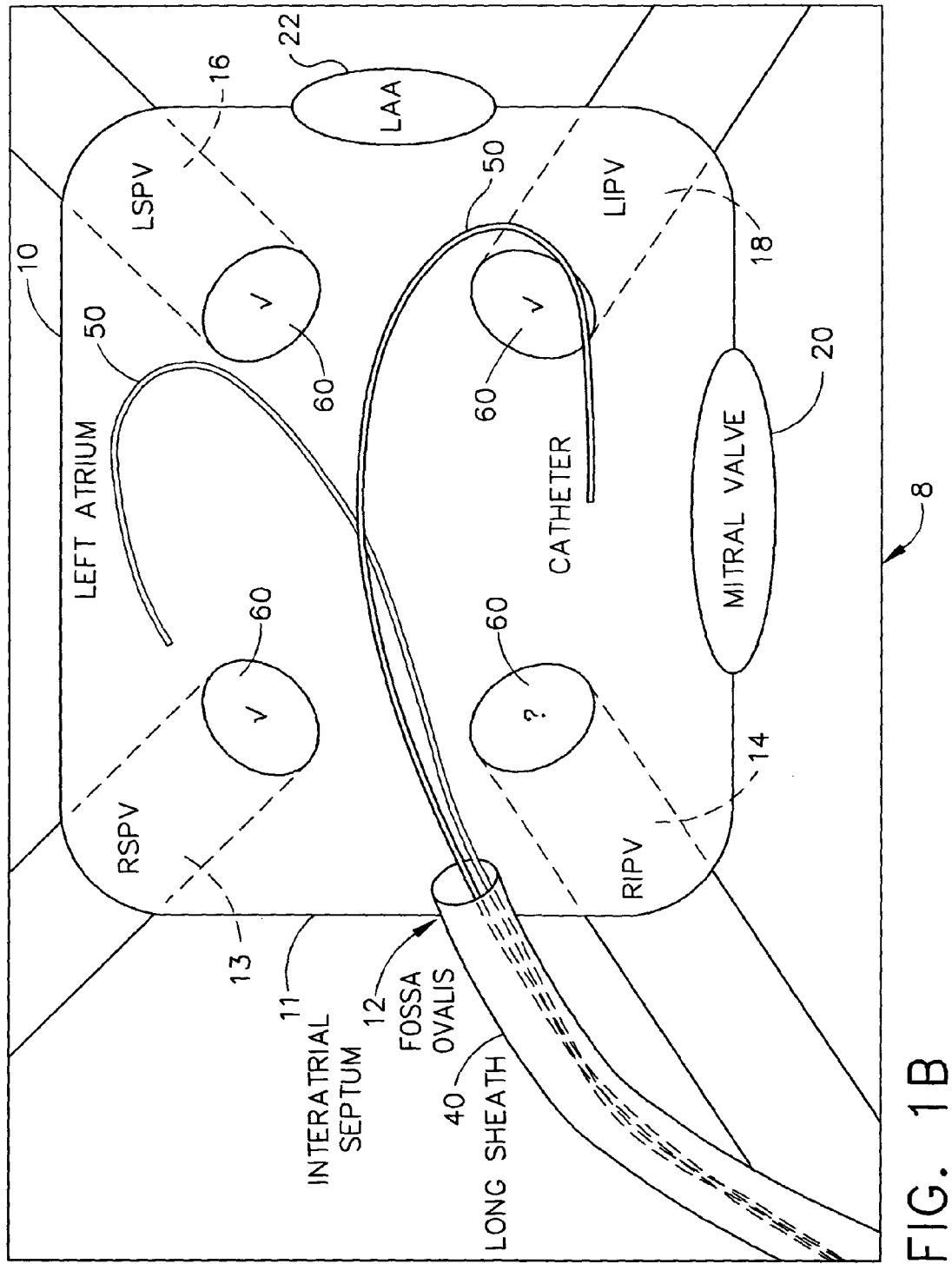
FIG. 1B is a schematic illustration of the method of FIG. 1A on a display for simulating, planning and implementing a cardiac procedure in the left atrium in accordance with the present invention.

FIGS. 1A and 1B illustrate a novel method, generally designated 100, in accordance with the present invention for planning, simulating and conducting a medical procedure such as a cardiac treatment procedure. The method 100 in accordance with the present invention comprises step 105 of obtaining, acquiring or using images and/or maps or pre-acquired images and/or maps of the left atrium 10 (FIG. 1B)

in computer simulation of the process of left atrial ablation displayed on display 8. The image or map may include, for example, a three-dimensional (3D) ultrasound image, MRI image, CT image or the like or an electrical map or electroanatomical map such as provided by the CARTO™ mapping and navigation system (manufactured and sold by Biosense Webster, Inc. of Diamond Bar, Calif.), i.e. a CARTO™ map (which may be pre-registered with the image). The simulation and method 100 in accordance with the present invention can be used both in order to plan the medical procedure and to guide the physician in the course of carrying out the procedure. An exemplary scenario is described below.

Planning the Ablation Procedure

As best illustrated in FIG. 1A, in step 105, the physician acquires an image and/or map of the heart and marks key features 110 of the left atrium 10 (all shown in FIG. 1B), including the fossa ovalis (or foramen ovale) 12, ostia of the four pulmonary veins (right superior pulmonary vein "RSPV" 13, right inferior pulmonary vein "RIPV" 14, left superior pulmonary vein "LSPV" 16, and left inferior pulmonary vein "LIPV" 18), annulus of the mitral valve 20, and ostia of the left atrial appendage 22. Alternatively, computerized image recognition algorithms may identify some or all of these features. In step 115, the dimensions of these features or key features of left atrium 10 are measured or calculated. One dimension of these features that are calculated is the diameter for each key feature. In this example, the diameters of the features are calculated 115 and the next step 120 is to determine desired paths for treatment based on the calculated dimensions (in this example, diameters of the features). Accordingly, for an RF ablation procedure and treatment with an ablation catheter 50, the diameters of the key features are calculated for use in determining the paths of the ablation lines to be created by the ablation catheter 50.

Based on the image/map and anatomical landmarks (key features) identified in steps 110 and 115, pathways for treatment are determined 120 and a computer simulates the process of inserting the sheath 40 (step 125) from the vena cava, through the right atrium and interatrial septum 11 through fossa ovalis/foramen ovale 12, into the left atrium 10 as shown in FIG. 1B. This step 125 allows the angle of attack and penetration depth of the sheath 40 to be determined in advance, in order to avoid injury to the patient during actual penetration of the septum 11.

Figure 2A:
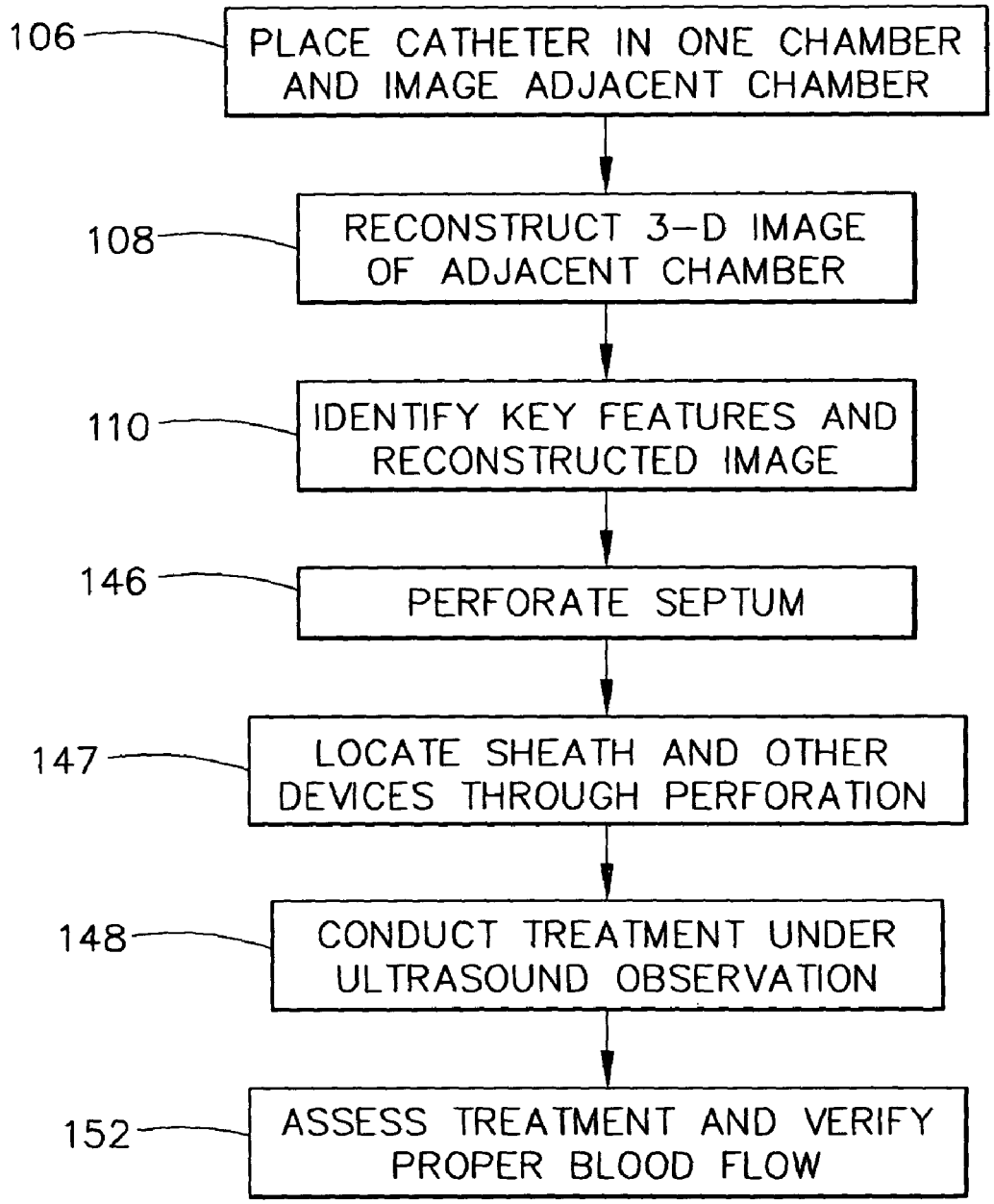
FIG. 2A is a flow chart illustrating a method for conducting a cardiac procedure using ultrasound guidance in accordance with a second embodiment of the present invention.
Figure 2B:
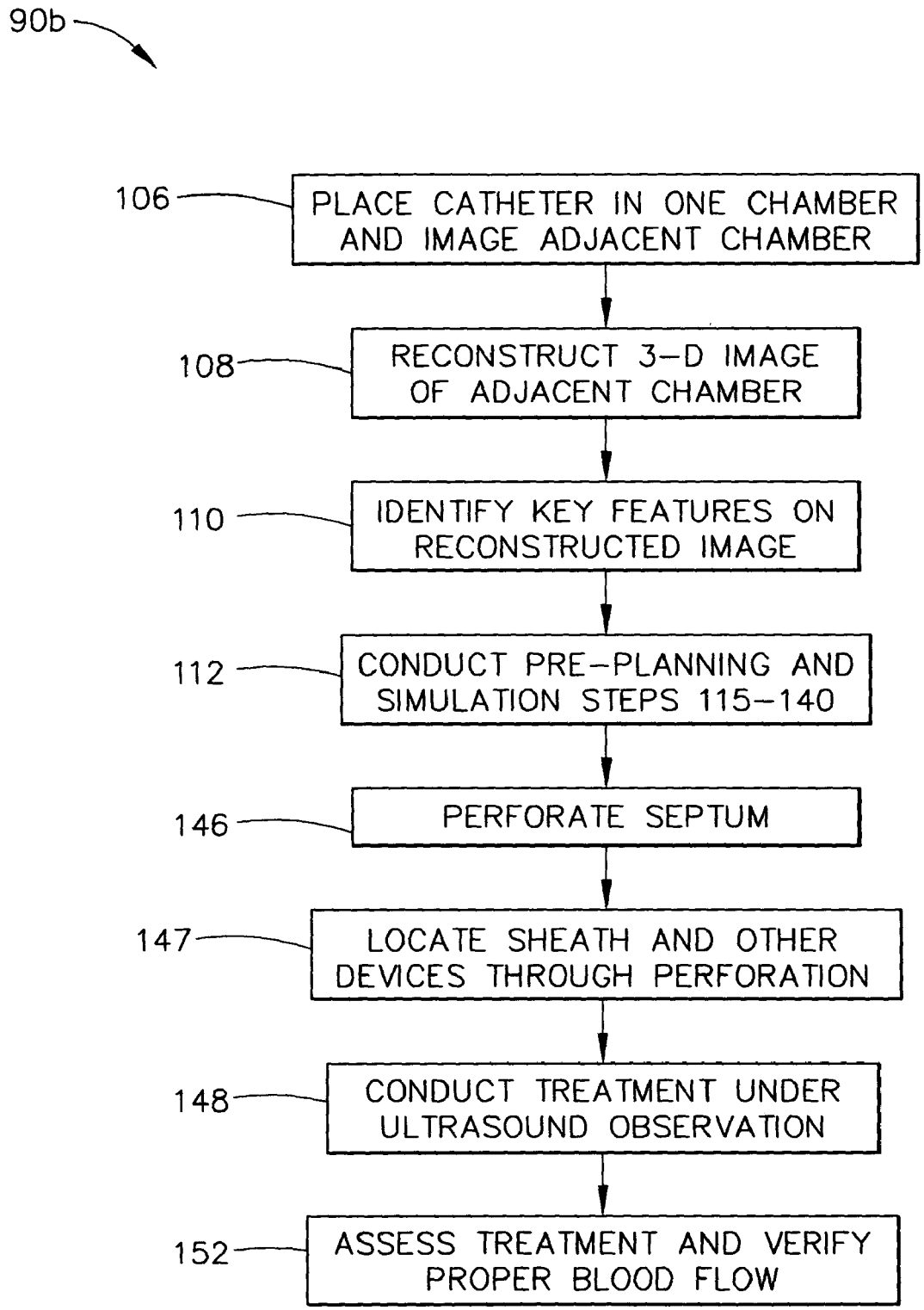
FIG. 2B is a flow chart illustrating a method for simulating, planning and conducting a cardiac procedure using ultrasound guidance in accordance with a third embodiment of the present invention.
Figure 2C:
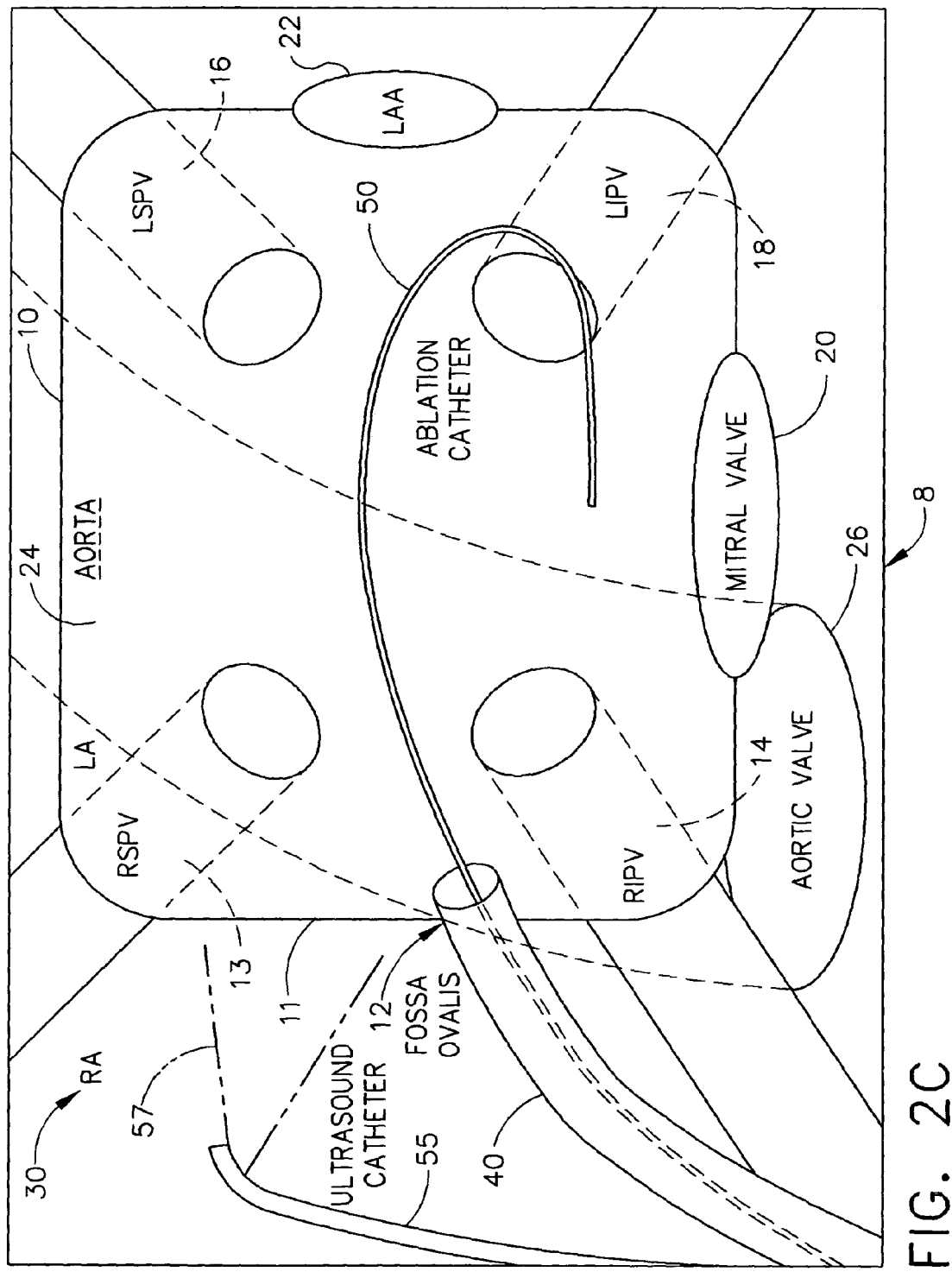
FIG. 2C is a schematic illustration of the methods of FIGS. 2A and 2B on a display for simulating, planning and implementing a cardiac procedure using ultrasound guidance in accordance with the present invention.
Figure 3A:
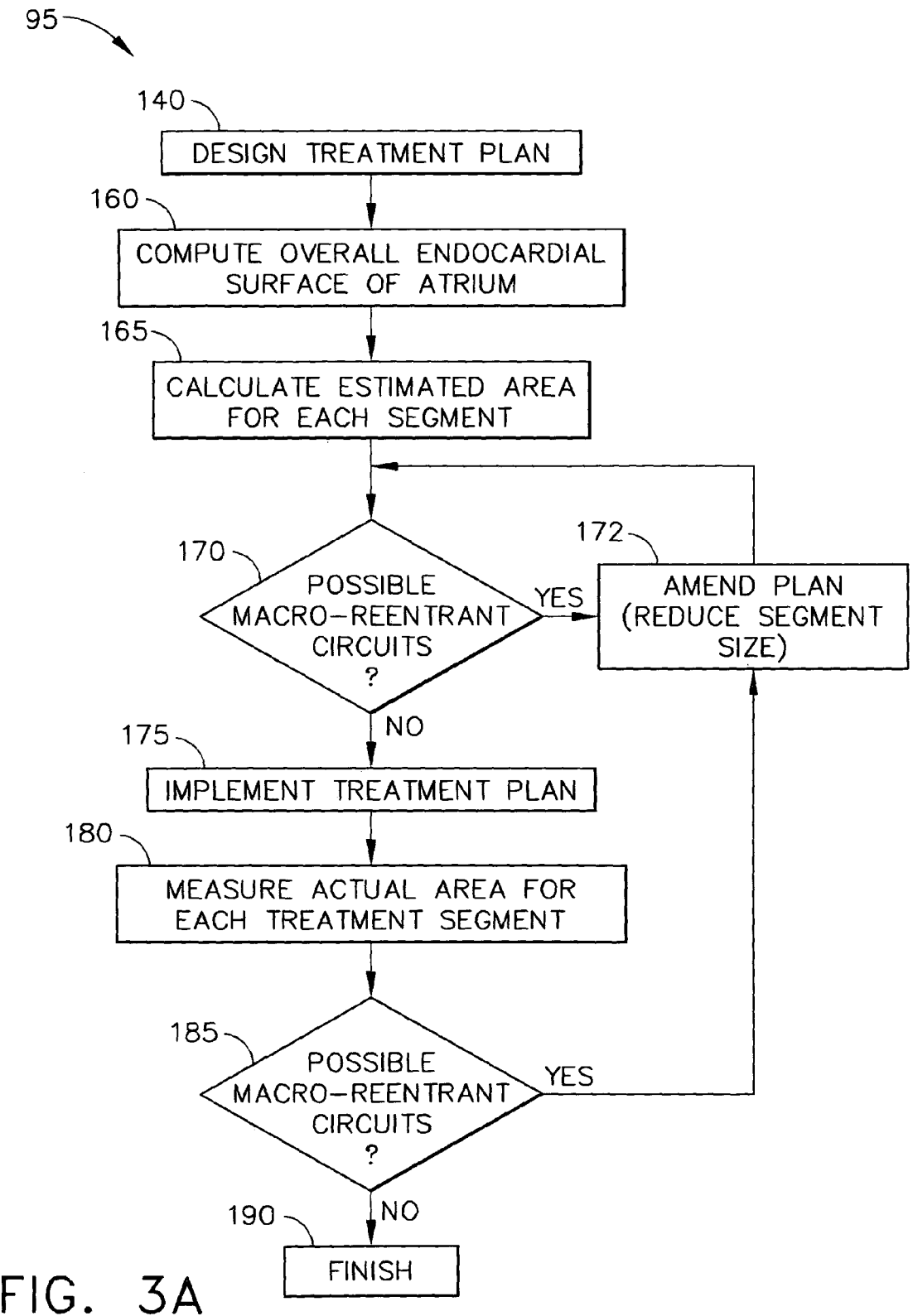
FIG. 3A is a flow chart illustrating a method for simulating, planning and conducting a cardiac procedure in order to prevent macro-reentrant circuits in accordance with a fourth embodiment of the present invention.
Figure 3B:
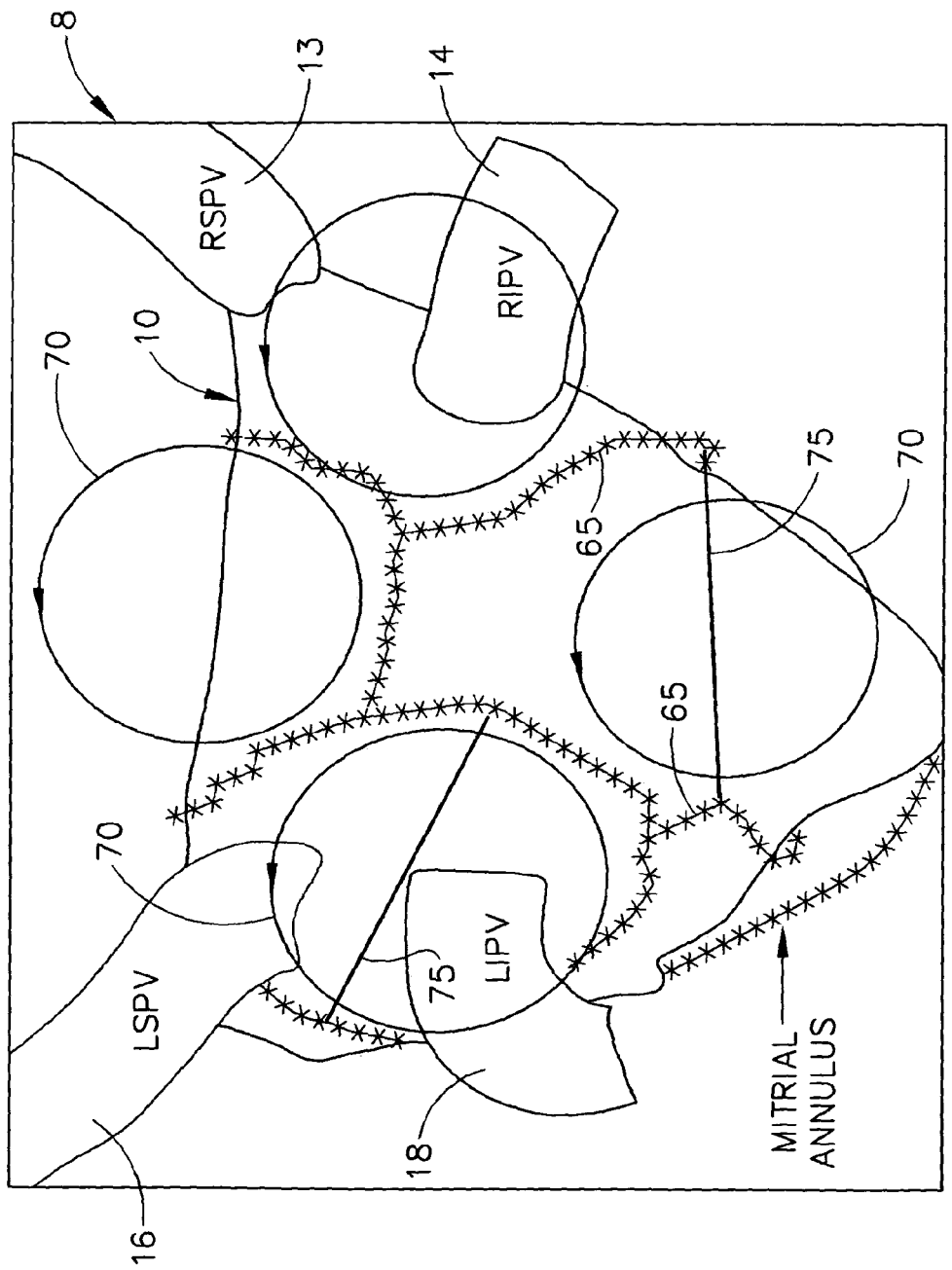
FIG. 3B is a schematic illustration of the method of FIG. 3A on a display for simulating, planning and implementing a cardiac procedure while preventing macro-reentrant circuits in accordance with the present invention.

The computer used for all embodiments of the present invention set forth in this disclosure comprises signal processing circuits with software and algorithms and is graphically represented in FIGS. 1B, 2C and 3B as display 8. Display 8 is also used to depict images and/or maps as well as the simulations and planning steps to include graphic representations of medical devices such as sheaths 40, ablation catheters 50, ultrasound imaging catheters 55, etc.

In step 130, the computer is used to simulate insertion of selected ablation catheters 50 through the sheath 40. Typically, a range of different catheters 50 are available wherein each catheter 50 is characterized by a certain radius of curvature as best shown in FIG. 1B. As illustrated in FIG. 1B, a catheter 50 of a certain curvature, after insertion through the sheath 50, is shown in two different orientations on display 8, which are separated by approximately 180° of rotation. The computer is then used to simulate the operation of a number of different degrees of freedom in order to ascertain the ability of the catheter 50 to reach all the of desired points that must be ablated in the left atrium (one or more points targeted for treatment such as ablation).

Additionally, computer simulation is also used for determining possible trajectories of the catheter 50 against the atrial wall of left atrium 10, depending on the depth of insertion and the orientation angle of the catheter 50 into the left atrium 10, along with the mechanical properties and mechanical effect of the atrial wall (with which the catheter 50 is in contact) on a particular trajectory of the catheter 50. Moreover, computer simulation is also used to determine the effect of the depth of extension of the sheath 40 into the left atrium 10 may have on the catheter trajectory. Steps 130 and 135 can be performed for different catheters 50 having different radii of curvature.

At the discretion of the physician, these steps are used to choose an optimal catheter 50 and to conduct step 135 which is to verify that the catheter 50 will be able to access all points in the left atrium that are to be ablated (one or more points in the left atrium to be treated). As best illustrated in FIG. 1B, indicia 60, such as symbols, labels, annotations or check marks, are identified directly on display 8. In this example, check marks are used as indicia 60 at the graphic representations of RSPV 13, LSPV 16 and LIPV 18 on display 8, indicating that the selected catheter 50 will be able to trace and form ablation lines around these features, while indicia 60 in the form of a question mark symbol is shown on the RIPV 14 graphic representation on display 8 as a feature that may be inaccessible using the selected catheter 50.

Based on the selected catheter 50 and on the features and their dimensions of the cardiac anatomy, the physician and/or computer (physician with or without the aid of computer and simulation software and algorithm) designs the ablation plan 140 for this patient by marking the one or more points to be treated such as through tracing the lines in the left atrium 10 that are to be ablated. The computer then calculates the execution parameters, such as the RF power, electrode type and burn duration, that are required to achieve complete transmural ablation without danger of puncturing the heart wall or causing collateral damage to extracardiac structures like the esophagus. These parameters may be based on the tissue thickness, as given by the 3D image of the heart.

Execution of the Procedure

The computer is programmed to give the physician instructions in the course of the procedure, based on the ablation plan 140 and execution parameters as previously determined (outlined above). The treatment (ablation) plan is then implemented 145. And, in step 150, the computer monitors execution of the procedure by tracking the position of the catheter 50 (and the sheath 50 if so desired), using suitable position sensors such as the electromagnetic position sensors used in the CARTO™ mapping and navigation system (not shown). Accordingly, in step 150, the computer can instruct the physician as to where and when to start and stop ablating, as well as where and at what angle to push the sheath 40 through the septum 11. In step 150, the computer can also provide real time guidance to the physician in step 145 (conducting and implementing the ablation plan) by guiding and cautioning the physician, i.e. provide a warning to the physician, as to possible dangerous conditions and deviations from the ablation plan 140.

The method according to the present invention is shown in FIGS. 1A and 1B, is particularly useful for acquiring an anatomical model (of the heart, particularly the left atrium 10); simulating an invasive procedure based on the anatomical model and on known properties of an instrument (or instruments) that is to be used in the procedure; and tracking the position of the instrument using a position sensor, in order to guide the actual procedure based on the simulated procedure outlined above.

This method in accordance with the present invention is particularly advantageous in that it permits accurate pre-planning of complex procedures, in order to find an optimal choice of tools (medical devices or medical instruments) and maneuvers, i.e. use thereof, that are expected to give a successful result, followed by monitoring, guidance and validation of the actual procedure to ensure that the result complies with the simulation.

Additionally, the method described above may also be used under robotic control; for instance, in a closed-loop control manner using robotically controlled and commanded instruments for catheter navigation and ablation.

Although this method of according to the present invention is particularly suited for treatment of atrial fibrillation by ablation of the left atrium 10, the principles of the invention may be applied for the treatment of ventricular tachycardia by ablating around a scar in the left ventricular wall, or for cell-based or gene-based therapies by injection catheter, as well as in all other medical applications such as invasive procedures in the fields of orthopedics, urology, neurology, thoracic, gastrointestinal, vascular, etc.

The present invention is also directed to a novel systematic method for carrying out ablation treatment of atrial fibrillation in the left atrium as best illustrated in FIGS. 2A, 2B and 2C. This method in accordance with present invention is conducted under ultrasound guidance using an ultrasound catheter 55 (FIG. 2C) placed in the right atrium 30 of the patient's heart. Ultrasound catheter 55 can include a position sensor, such as an electromagnetic position sensor as disclosed in U.S. patent application Ser. No. 11/114,847 filed Apr. 26, 2005, which is incorporated by reference herein. Thus, in this embodiment, the ultrasound catheter 55 with position sensor is used in conjunction with a location system having a computer and signal processing circuits for determining the accurate location of the position sensor and catheter 55 and navigating the catheter 55 in the patient's body.

In this exemplary embodiment, the steps of the procedure 90a are schematically illustrated in FIG. 2A and outlined below. First, in step 106, the physician places ultrasound catheter 55 in one chamber of the patient's heart and obtains one or more images of an adjacent chamber using the ultrasound catheter 55. For example, the physician inserts ultrasound catheter 55 into the right atrium 30 (FIG. 2C) and aims the ultrasound beam 57 projected from catheter 55 at an adjacent chamber, for instance, the left atrium 10 and uses the catheter 55 to acquire ultrasound images (two-dimensional "2D" ultrasound images) of the left atrium 10 and surrounding structures. The position sensor (not shown) used on the ultrasound catheter 55 and its associated location system (not shown) allow for accurate location determination (determination of position coordinates and orientation coordinates) of the position sensor and catheter 55. For example, the position sensor allows for a portion of catheter 55 to be accurately tracked and navigated using three dimensions of position coordinates (X, Y and Z coordinate axis directions) and at least two dimensions of orientation coordinates (yaw and pitch) to include up to three dimensions of orientation coordinates (yaw, pitch and roll). Accordingly, since the location coordinates (position coordinates and orientation coordinates) for a portion of the catheter 55 are determined using a location system (not shown) operatively connected to the position sensor of the catheter 55, three-dimensional ultrasound slices are obtained using the 2D ultrasound images and their associated location coordinates for each pixel of each respective 2D ultrasound image.

Thus, the computer uses the location coordinates (position coordinates and orientation coordinates) for each pixel of each 2D ultrasound image and makes a resulting three-dimensional ultrasound image slice. Then, in step 108, the three-dimensional ultrasound image slices acquired by the catheter 55 and generated by the computer are also used by the computer (having reconstruction algorithms and reconstruction software) to reconstruct a 3D ultrasound image reconstruction (3D model or 3D reconstructed image) of the left atrium 10. In addition, the reconstructed 3D ultrasound image model or reconstruction will include the aortic valve 26 and the ascending aorta 24, located behind the left atrium 10.

In the next step 110, key features such as landmarks are identified on the 3D reconstructed image, either automatically or interactively, by the physician. These landmarks include the planes and outlines of the fossa ovalis (or foramen ovale) 12 and the aortic valve 26, as well as the aorta itself 24. Other key landmarks typically include the ostia of the four pulmonary veins (right superior pulmonary vein "RSPV" 13, right inferior pulmonary vein "RIPV" 14, left superior pulmonary vein "LSPV" 16, and left inferior pulmonary vein "LIPV" 18), annulus of the mitral valve 20, and ostia of the left atrial appendage 22.

In preparation for inserting the ablation catheter 50 from the right atrium 30 into the left atrium 10, in step 146 (FIG. 2A) the physician pierces the septum 11 at the fossa ovalis 12 using a needle or the sheath 40 as shown in FIG. 2C. The locations of the aortic valve 26 and aorta 24 in the 3D ultrasound image are indicated to ensure that the physician does not accidentally pierce the aorta 24 with the needle. The system and computer can be programmed to automatically guide the physician as to the correct direction and depth for insertion of the needle through the septum 11. The ultrasound catheter 55 may be used in Doppler mode to observe creation of the hole in the septum 11 by detecting the flow of blood through the hole from the left atrium 10 to the right atrium 30.

In step 147, the ablation catheter 50 (and any other desired medical devices if needed for the procedure) is inserted (through the sheath 40) into the left atrium 10 in order to create the desired ablation pattern. In step 148, the ultrasound catheter 50 remains positioned only in the right atrium 30 and is used to image 57 the area of the tip of the ablation catheter 50 (located in the left atrium 10) in order to observe and image the results of ablation in real time. The ultrasound catheter 55 or/and the ablation catheter 50 may be automatically controlled, for instance under robotic control, so that the 2D ultrasound fan or projection 57 tracks the location of the ablation catheter 50 as the ablation catheter 50 moves within the left atrium 10. After completion of the treatment step, i.e. ablation step (under ultrasound guidance) in step 148, the ultrasound catheter 55 captures further ultrasound images of the left atrium 10 for the purpose of lesion assessment and to ensure that blood flow through the pulmonary veins 13, 14, 16 and 18 has not been compromised in step 152. Thus, step 152 is used to assess the level of treatment provided and to verify proper blood flow through the chambers of the heart and key vessels such as the pulmonary veins 13, 14, 16 and 18.

This method according to the present invention is particularly advantageous in that it enhances the precision and safety of ablation treatment for left atrial fibrillation, by means of a novel combination of intracardiac ultrasound imaging, position sensing, preplanning, simulation and guidance (discussed in greater detail below).

Another embodiment of this method 90b in accordance with the present invention is illustrated in FIG. 2B and uses many of the steps outlined for the method 90a (FIG. 2A), and likewise the same reference numerals are used for the same method steps. However, an additional step, generally designated 112, is the pre-planning and simulation step, which are the same steps: calculating dimensions of features 115, determining paths for treatment 120, simulation the sheath insertion process 125, simulation of devices inserted through the sheath 130, verifying access to all points to be treated 135, designing the treatment plan 140, and monitoring procedure and providing guidelines 150 illustrated in FIG. 1A and outlined in detail previously above.

Additionally, these methods described above and illustrated in FIGS. 2A and 2B may also be used under robotic control, for instance, in a closed-loop control manner using robotically controlled and commanded instruments for catheter navigation and ablation.

Although the methods of the present invention illustrated in FIGS. 2A and 2B are particularly suited for treatment of atrial fibrillation by ablation of the left atrium, the principles of the invention may be applied in the ventricles and in other sorts of invasive procedures performed on other body organs such as those briefly identified previously by way of example.

Another method in accordance with the present invention is directed to treating atrial fibrillation in the heart through a novel and efficient method for preventing macro-reentrant circuits from occurring the atrial wall of the heart. As is well known, catheter-based treatments of left-atrial fibrillation generally involve ablation of myocardial tissue in a pattern that is designed to encircle, and thus isolate, the orifices of the pulmonary veins. This pattern of treatment is based on work (by known Electrophysiologist Dr. Haissaguerre and his colleagues) showing that atrial fibrillation is usually induced by stimulation from a site within the orifice of one or more of the pulmonary veins. Treatment of this sort, however, has an unacceptably high failure rate when used as the sole treatment for atrial fibrillation that is typically around 30% failure rate.

It is postulated that the reason for this high failure rate is that chronic atrial fibrillation does not require any sort of induction stimulus. Rather, as shown by the work of known electrophysiologists Dr. Wijffels and Dr. Allessie, once the atria begin to fibrillate, they undergo a process of electrical "remodeling," which causes fibrillation to continue even in the absence of a specific induction site.

Accordingly, the method in accordance with the present invention is directed to ablation treatment for treating atrial fibrillation that is not only directed to isolating induction sites, such as the ostia of the pulmonary veins (right superior pulmonary vein "RSPV" 13, right inferior pulmonary vein "RIPV" 14, left superior pulmonary vein "LSPV" 16, and left inferior pulmonary vein "LIPV" 18 shown in FIG. 3B), but also to prevent macro-reentrant circuits 70 from occurring within the atrial wall itself in left atrium 10.

The physical size of these macro-reentrant circuits 70 is determined by the duration of the refractory period at any given site in the atria. Normally, atrial refractory periods are long (average duration of refractory period under normal conditions in a time range of 120-150 msec.), and the macro-reentrant circuits are consequently large (typically greater than 6-7 cm in diameter).

In atrial fibrillation, however, the refractory period may be much shorter, i.e. in a time range from 80-100 msec., so that the macro-reentrant circuits 70 may be small enough to survive between the actual ablation lines 65, i.e. macro-reentrant circuits 70 as small as 1 cm in diameter. The circular paths marked 70 between the ablation lesions 65 shown in FIG. 3B illustrate this situation. This problem becomes more difficult to manage the larger the volume of the atria and surface area of the atrial endocardium.

In response to this problem, the present invention offers a novel method 95 for preventing macro-reentrant circuits 70 (FIG. 3B) in the treatment of atrial fibrillation as schematically shown in FIG. 3A. In accordance with the method 95 of the present invention, the first step 140 is to design a treatment plan, i.e. designing an ablation strategy (that includes both pulmonary vein isolation and the ablation lines required for proper isolation and block) on the surface of the atrium 10 using a pre-acquired 3D image (such as CT, MR and/or ultrasound) image. Again, the development of the treatment strategy (outlined in step 140) can also include the general pre-planning and simulation step 112 of FIG. 1A such as one or more of individual steps to include step 105 acquiring an image and/or map of the surface or portion of the heart such as the atrium or portion of the atrium or other chamber or vessel; and displaying the image and/or map of the surface or portion of the heart or atrium on the display 8 (FIG. 3B); step 110 marking at least one feature on the image and/or map (such as one or more key features to include anatomical landmarks); step 115 calculating dimensions of the one or more key features to include determining the diameter for each of the key features, and identifying one or more points on or within the heart for treatment as part of a treatment plan; step 120 determining the pathways for treatment; step 125 simulating insertion of the sheath 40; step 130 simulating insertion of other medical devices, such as ablation catheters, through the sheath and into the heart and atrium; step 135 verifying that the one or more points on or within the heart can be accessed for treatment; and step 140 designing the treatment plan wherein each of these steps can be used in any combination or sequence. Details of these steps have also been described previously above.

As schematically shown in FIG. 3A, after the treatment strategy has been developed and outlined in the treatment plan step 140, the overall endocardial surface area of the atrium 10 is computed in step 160. For purposes of the present invention, step 160 is also directed to computing any portion of the endocardial surface area and not just the entire surface area of the endocardium surface, but rather any surface or portion of surface of interest. After computing the endocardial surface of the atrium, the estimated area of each segment is calculated following the planned ablation pattern in step 165. Representative examples of segments are illustrated in FIG. 3B and are the areas between lines of ablation 65, i.e. non-ablated areas between ablation lines 65. Then, in step 170 each segment (non-ablated area or estimated area not treated as part of the designed treatment plan) is assessed to determine whether or not it is possible for each segment to harbor or likely to experience macro-reentrant circuits 70. Step 170 is conducted over a range of likely refractory periods such as the refractory period ranges outlined previously above (or set by the user—if known). If it is likely that one or more of the segments may still be large enough to harbor macro-reentrant circuits, then the therapeutic plan is amended or modified (step 172) to reduce the areas of the segments, i.e. reduce the segment size by planning for additional ablation lines or lines of block designated by reference numeral 75 in FIG. 3B. And, step 170 is conducted again in order to determine if the reduced segment (segment with a smaller area or size now defined by additional lines of ablation 75) is capable of harboring or experiencing macro-reentrant circuits 70.

In the event that the segment size is sufficient in size or are such that it is not capable of harboring or experiencing macro-reentrant circuits 70, then the treatment plan is implemented and the therapy, such as ablation treatment, is provided by the physician in step 175.

Again, execution the therapeutic plan at step 175 can be conducted manually (by the physician) or under robotic control. After executing the treatment plan, the actual area of each segment is measured in step 180. In step 180, the measurement of the actual area of each segment created after ablation lines 65 have been made (including implementing the planned lines of ablation 75 for a reduced segment size) is normally conducted at the end of the procedure. However, in step 185, if measurement of the actual segment size or actual segment area reveals that it is still possible for macro-reentrant circuits to exist, then the therapeutic plan is amended or revised at step 172 in an effort to reduce the segment size in a manner that is incapable of experiencing macro-reentrant circuits. And, the amended plan will be implemented at step 175 with the remainder of steps 180 and 185 conducted again.

In the event that the measurement of the actual segment size or actual segment area at step 180 reveals that it is not possible for macro-reentrant circuits to exist (analysis conducted at step 185), then the procedure is considered completed or finished (step 190 indicating that the procedure is complete).

As noted above, additional ablation lines 75 are added to the original ablation pattern 65 (either in the planning stage at step 170 and 172 or after the first stage of execution at step 185 and 172) in order to cut segments that may still be large enough to sustain macro-reentrant circuits.

As is well known, the prior art and current surgical and catheter-based treatments for atrial fibrillation use approximately the same lesion pattern for all patients and, as a consequence, these procedures at patients suffer from high failure rates. The present invention solves this problem by providing a systematic way to tailor the treatment to the anatomical and electrophysiological characteristics of each specific patient, based on quantitative measures taken from images and/or maps of the heart in question. Thus, it is believed that this novel approach, system and method will increase the success rate of atrial fibrillation treatment.

Inasmuch as the foregoing specification comprises preferred embodiments of the invention, it is understood that variations and modifications may be made herein, in accordance with the inventive principles disclosed, without departing from the scope of the invention.

While preferred embodiments of the present invention have been shown and described herein, it will be obvious to those skilled in the art that such embodiments are provided by way of example only. Numerous variations, changes and substitutions will now occur to those skilled in the art without departing from the invention. Accordingly, it is intended that the invention be limited only by the spirit and scope of the appended claims.

What is claimed is:

1. A method for pre-planning a cardiac procedure on a heart comprising the steps of:
   acquiring an image or map of the heart;
   displaying the image or map of the heart;
   marking at least one feature on the image or map;
   calculating dimensions of the at least one feature;
   identifying one or more points on or within the heart for treatment;
   determining paths based on the at least one marked feature and the dimensions of the at least one marked feature to the one or more points on or within the heart for treatment;
   simulating insertion of a sheath into the heart through one of the paths;
   simulating insertion of a medical device through the sheath and within the heart;
   verifying that the one or more points on or within the heart can be accessed by the medical device for treatment;
   measuring a penetration depth of the sheath in the heart using the step of simulating insertion of the sheath;
   verifying that the penetration depth does not exceed a specified measurement;
   confirming that the insertion of the sheath avoids injury to the heart at the penetration depth of the sheath using the step of simulating insertion of the sheath; and
   simulating insertion of selected ablation catheters through the sheath.

2. The method of claim 1, further comprising:
   selecting ablation catheters having different radii of curvature for the step of simulating insertion of the selected ablation catheters through the sheath; and
   determining the paths to the heart of the ablation catheters in relation to the penetration depth of the sheath.

3. A method for developing a plan for a cardiac procedure comprising the steps of
   acquiring an image or map of the heart;
   displaying the image or map of the heart;
   marking at least one feature on the image or map;
   calculating dimensions of the at least one feature;
   identifying one or more points on or within the heart for treatment;
   determining paths based on the at least one marked feature and the dimensions of the at least one marked feature to the one or more points on or within the heart for treatment;
   simulating insertion of a sheath into the heart through one of the paths;
   simulating insertion of a medical device through the sheath and within the heart; and
   verifying that the one or more points on or within the heart can be accessed by the medical device for treatment;
   measuring a penetration depth of the sheath in the heart using the step of simulating insertion of the sheath;
   verifying that the penetration depth does not exceed a specified measurement;
   confirming that the insertion of the sheath avoids injury to the heart at the penetration depth of the sheath using the step of simulating insertion of the sheath; and
   simulating insertion of selected ablation catheters through the sheath.

4. A method for pre-planning and performing a cardiac procedure on a heart comprising the steps of:
   acquiring an image or map of the heart;
   displaying the image or map of the heart;
   marking at least one feature on the image or map;
   calculating dimensions of the at least one feature;
   identifying one or more points on or within the heart for treatment;
   determining paths based on the at least one marked feature and the dimensions of the at least one marked feature to the one or more points on or within the heart for treatment;
   simulating insertion of a sheath into the heart through one of the paths;
   simulating insertion of a medical device through the sheath and within the heart;
   verifying that the one or more points on or within the heart can be accessed by the medical device for treatment;
   performing a medical procedure on or within the heart;

measuring a penetration depth of the sheath in the heart using the step of simulating insertion of the sheath;
verifying that the penetration depth does not exceed a specified measurement;
confirming that the insertion of the sheath avoids injury to the heart at the penetration depth of the sheath using the step of simulating insertion of the sheath; and
simulating insertion of selected ablation catheters through the sheath.

5. The method according to claim 4, wherein the medical procedure is monitored and guided according to the plan.

6. The method according to claim 5, wherein the medical procedure is monitored and robotically guided according to the plan.

7. A method for developing a plan and performing a cardiac procedure on a heart comprising the steps of:
acquiring an image or map of the heart;
displaying the image or map of the heart;
marking at least one feature on the image or map;
calculating dimensions of the at least one feature;
identifying one or more points on or within the heart for treatment;
determining paths based on the at least one marked feature and the dimensions of the at least one marked feature to the one or more points on or within the heart for treatment;
simulating insertion of a sheath into the heart through one of the paths;
simulating insertion of a medical device through the sheath and within the heart;
verifying that the one or more points on or within the heart can be accessed by the medical device for treatment;
performing a medical procedure on or within the heart;
measuring a penetration depth of the sheath in the heart using the step of simulating insertion of the sheath;
verifying that the penetration depth does not exceed a specified measurement;
confirming that the insertion of the sheath avoids injury to the heart at the penetration depth of the sheath using the step of simulating insertion of the sheath; and
simulating insertion of selected ablation catheters through the sheath.

8. The method according to claim 7, wherein the medical procedure is monitored and guided according to the plan.

9. The method according to claim 8, wherein the medical procedure is monitored and robotically guided according to the plan.

10. A method for simulating a cardiac procedure on a heart comprising the steps of:
acquiring an image or map of the heart;
displaying the image or map of the heart;
marking at least one feature on the image or map;
calculating dimensions of the at least one feature;
identifying one or more points on or within the heart for treatment;
determining paths based on the at least one marked feature and the dimensions of the at least one marked feature to the one or more points on or within the heart for treatment;
simulating insertion of a sheath into the heart through one of the paths;
simulating insertion of a medical device through the sheath and within the heart;
verifying that the one or more points on or within the heart can be accessed by the medical device for treatment;
measuring a penetration depth of the sheath in the heart using the step of simulating insertion of the sheath;
verifying that the penetration depth does not exceed a specified measurement;
confirming that the insertion of the sheath avoids injury to the heart at the penetration depth of the sheath using the step of simulating insertion of the sheath; and
simulating insertion of selected ablation catheters through the sheath.

11. A method for simulating and developing a plan for a cardiac procedure comprising the steps of:
acquiring an image or map of the heart;
displaying the image or map of the heart;
marking at least one feature on the image or map;
calculating dimensions of the at least one feature;
identifying one or more points on or within the heart for treatment;
determining paths based on the at least one marked feature and the dimensions of the at least one marked feature to the one or more points on or within the heart for treatment;
simulating insertion of a sheath into the heart through one of the paths;
simulating insertion of a medical device through the sheath and within the heart;
verifying that the one or more points on or within the heart can be accessed by the medical device for treatment;
measuring a penetration depth of the sheath in the heart using the step of simulating insertion of the sheath;
verifying that the penetration depth does not exceed a specified measurement;
confirming that the insertion of the sheath avoids injury to the heart at the penetration depth of the sheath using the step of simulating insertion of the sheath; and
simulating insertion of selected ablation catheters through the sheath.

12. A method for simulating and performing a cardiac procedure on a heart comprising the steps of:
acquiring an image or map of the heart;
displaying the image or map of the heart;
marking at least one feature on the image or map;
calculating dimensions of the at least one feature;
identifying one or more points on or within the heart for treatment;
determining paths based on the at least one marked feature and the dimensions of the at least one marked feature to the one or more points on or within the heart for treatment;
simulating insertion of a sheath into the heart through one of the paths;
simulating insertion of a medical device through the sheath and within the heart;
verifying that the one or more points on or within the heart can be accessed by the medical device for treatment;
performing a medical procedure on or within the heart;
measuring a penetration depth of the sheath in the heart using the step of simulating insertion of the sheath;
verifying that the penetration depth does not exceed a specified measurement;
confirming that the insertion of the sheath avoids injury to the heart at the penetration depth of the sheath using the step of simulating insertion of the sheath; and
simulating insertion of selected ablation catheters through the sheath.

13. The method according to claim 12, wherein the medical procedure is monitored and guided according to the plan.

14. The method according to claim 13, wherein the medical procedure is monitored and robotically guided according to the plan.

15. A method for simulating a cardiac procedure, developing a plan and performing a cardiac procedure on a heart comprising the steps of:
    acquiring an image or map of the heart;
    displaying the image or map of the heart;
    marking at least one feature on the image or map;
    calculating dimensions of the at least one feature;
    identifying one or more points on or within the heart for treatment;
    determining paths based on the at least one marked feature and the dimensions of the at least one marked feature to the one or more points on or within the heart for treatment;
    simulating insertion of a sheath into the heart through one of the paths;
    simulating insertion of a medical device through the sheath and within the heart;
    verifying that the one or more points on or within the heart can be accessed by the medical device for treatment;
    performing a medical procedure on or within the heart;
    measuring a penetration depth of the sheath in the heart using the step of simulating insertion of the sheath;
    verifying that the penetration depth does not exceed a specified measurement;
    confirming that the insertion of the sheath avoids injury to the heart at the penetration depth of the sheath using the step of simulating insertion of the sheath; and
    simulating insertion of selected ablation catheters through the sheath.

16. The method according to claim 15, wherein the medical procedure is monitored and guided according to the plan.

17. The method according to claim 16, wherein the medical procedure is monitored and robotically guided according to the plan.

* * * * *